(12) United States Patent
Zar et al.

(10) Patent No.: US 12,241,120 B2
(45) Date of Patent: Mar. 4, 2025

(54) BAG AND BOX APPARATUS WITH FARADAY BAG AND SELF-CLOSING RF-TIGHT DEVICE PASSAGE FOR RECOVERING, TEMPORARILY STORING, AND THEN RETURNING FREIGHT-TRACKING TRANSMITTERS

(71) Applicant: SLNT INC., Sheridan, WY (US)

(72) Inventors: Aaron Zar, Aptos, CA (US); Byron Brodowicz, Sheridan, WY (US)

(73) Assignee: SLNT INC, Sheridan, WY (US)

( * ) Notice: Subject to any disclaimer, the term of this patent is extended or adjusted under 35 U.S.C. 154(b) by 335 days.

(21) Appl. No.: 17/955,313

(22) Filed: Sep. 28, 2022

(65) Prior Publication Data

US 2023/0102853 A1    Mar. 30, 2023

Related U.S. Application Data

(60) Provisional application No. 63/249,414, filed on Sep. 28, 2021.

(51) Int. Cl.
*B65D 85/00* (2006.01)
*B65D 77/06* (2006.01)
(Continued)

(52) U.S. Cl.
CPC ........... *C12Q 1/686* (2013.01); *B65D 77/062* (2013.01); *B65D 85/68* (2013.01); *B65D 2203/10* (2013.01); *B65D 2585/86* (2013.01)

(58) Field of Classification Search
CPC ........ B65D 33/24; B65D 43/16; B65D 85/68; B65D 77/062; B65D 2203/10;
(Continued)

(56) References Cited

U.S. PATENT DOCUMENTS 3,963,883 A * 6/1976 Kulka ..................... H04M 1/19
379/453
7,075,798 B2 * 7/2006 Hendrickson ........ H05K 9/0043
206/720

(Continued)

FOREIGN PATENT DOCUMENTS

RU         206230         3/2021

OTHER PUBLICATIONS

PCT International Preliminary Report on Patentability for PCT/US2022/045098 dated Apr. 11, 2024.

*Primary Examiner* — Luan K Bui
(74) *Attorney, Agent, or Firm* — Myers Andras Ashman Bisol LLP; Joseph C Andras

(57) ABSTRACT

A soft- or hard-sided apparatus for temporarily storing a plurality of electronic devices that transmit electromagnetic signals that would, if not suppressed, interfere with other electronic devices or make the devices accessible to outsiders. The apparatus includes a container, such as a soft-sided bag, that is sized for holding the plurality of electronic devices and is specially adapted to be normally RF-tight to suppress the electromagnetic signals transmitted by the plurality of electronic devices to prevent them from interfering with other electronic devices. The container further includes a small opening assembly in the container that opens and closes, such as a trap door, outfitted with magnets. The first small opening assembly is adapted to be RF-tight when closed so that a user can push an electronic device through the assembly, into the container, after which all the electronic devices are silenced inside of the container. The container further includes a second larger opening assembly to allow removal of all of the electronic devices as a group. The soft-sided container can be located in a cardboard shipping box, ready to be emptied nearby or returned to a (Continued)

third-party when full so that the devices can be refurbished and re-used.

27 Claims, 18 Drawing Sheets

(51) Int. Cl.
*B65D 85/68* (2006.01)
*C12Q 1/686* (2018.01)

(58) Field of Classification Search
CPC ............ B65D 2313/02; B65D 2313/04; B65D 2585/86; H04M 1/19; H05K 9/0043; H05K 1/0224; H05K 2201/0707
USPC .......... 206/305, 320, 719–721; 174/51, 350; 361/732, 752, 792, 799, 800, 816, 818; 455/36, 67.12, 130, 227, 226.1, 226.4
See application file for complete search history.

(56) References Cited

U.S. PATENT DOCUMENTS

| | | | |
|---|---|---|---|
| 8,699,235 B2* | 4/2014 | Soufan | H04M 1/19 |
| | | | 361/818 |
| 2003/0057131 A1* | 3/2003 | Diaferia | H05K 9/0049 |
| | | | 206/320 |
| 2007/0109130 A1 | 5/2007 | Edenfield | |
| 2009/0021654 A1* | 1/2009 | Jones | A45C 15/00 |
| | | | 348/836 |
| 2010/0230018 A1 | 9/2010 | Nielsen | |
| 2011/0198245 A1* | 8/2011 | Soufan | H04M 1/19 |
| | | | 206/216 |
| 2015/0052617 A1* | 2/2015 | Zar | B65D 33/00 |
| | | | 726/27 |

* cited by examiner

Typical Asset Tracking Devices 11
RF Interference Sources When in a Warehouse
One-Time Use
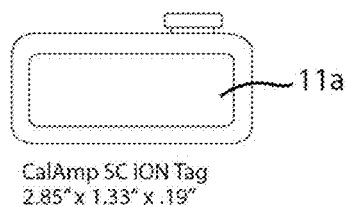
Re-usable
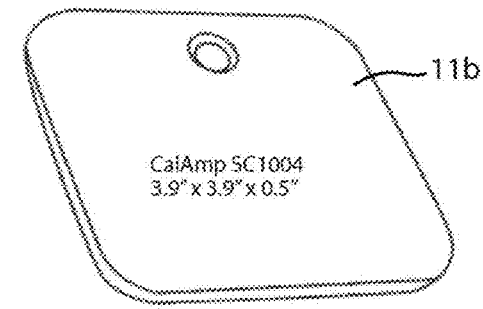
FIG. 1
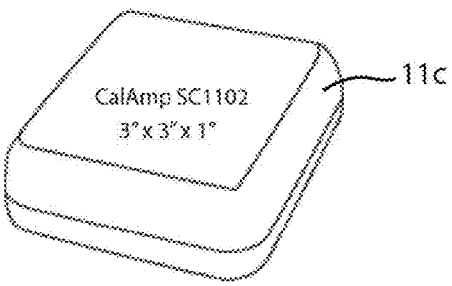
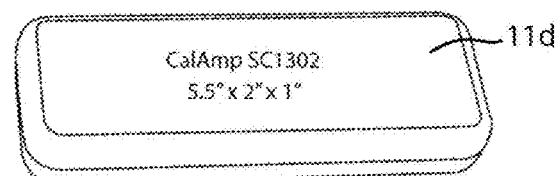
FIG. 2
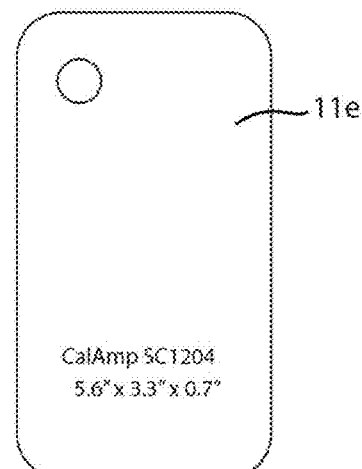

Presently Preferred Warehouse Bag
(Soft-Sided Container)

Warehouse Bag as shipped prior to assembly with storage / shipping box

Warehouse Bag removed from package

Presently Preferred Warehouse Bag

Warehouse Bag - expanded - trap door end - with Velcro strips surrounding trap door Warehouse Bag - expanded - other end Warehouse Bag - expanded - roll toward side with rolltop still open - with first Velcro strip visible Warehouse Bag - expanded - roll from side with rolltop still open - with second Velcro

Presently Preferred Warehouse Bag

Warehouse Bag - bottom - with Velcro

Warehouse Bag - rolltop closed - trapdoor end

Typical Box Suitable for Use with Warehouse Bag

FIG. 12
Appropriate Box for Bag

Typical Box Suitable for Use with Warehouse Bag

Appropriate Box for Warehouse Bag

Alternative Preparation of Box

Cut Flap in Box Instead of Hole

Connect Bag to Box
(preferably on bottom too)

Alternative Embodiment
(Hard-Sided Container)

BAG AND BOX APPARATUS WITH FARADAY BAG AND SELF-CLOSING RF-TIGHT DEVICE PASSAGE FOR RECOVERING, TEMPORARILY STORING, AND THEN RETURNING FREIGHT-TRACKING TRANSMITTERS

BACKGROUND

This application claims the benefit of provisional patent application No. 63/249,414, filed Sep. 28, 2021, the entire contents of which are hereby incorporated by reference.

FIELD OF THE INVENTION

The present invention relates generally to Faraday cages which are containers made of electrically conducting material that prevents electromagnetic signals (including radio frequency or RF signals) from entering or exiting the Faraday cage and, more particularly, to a bag-in-a-box apparatus which uniquely incorporates a Faraday cage system and a self-closing, electromagnetically-attenuating device passage for recovering freight-tracking devices, temporarily storing the freight-tracking devices, substantially silencing the freight-tracking devices so they do not interfere with other sensitive equipment in the location where they are being recovered, and then enabling the convenient and electromagnetically-attenuated return of the freight-tracking devices for restoration and reuse.

DESCRIPTION OF THE RELATED ART

Electromagnetic transmitters are everywhere. Our world is full of them. Some are active devices with a power source that can transmit radio frequency (RF) signals over relatively long distances (e.g. wireless mobile devices), and others are passive devices that get the energy needed to respond from an incoming RF signal and then transmit a low power response over a relatively short distance (e.g. credit cards with RFID tags).

Wireless mobile devices such as laptops, tablets and cell phones are examples of active devices that contain various RF emitters including cellular (2G, 3G, LTE, 5G etc.), WiFi, Bluetooth, Bluetooth LE (low energy), Near Field Communication (NFC) technology, etc.

Radio Frequency Identification (RFID) tags have also become common. They are often found in small personal items that can be queried at relatively close distance, e.g. credit cards, passports, driver's licenses, employee badges, automotive key fobs, toll road transponders, etc. The RFID tag is connected to a miniature antenna and is passively listening all the time. In use, if the RFID tag receives an electromagnetic signal at the correct frequency and in the correct digital format, it responds back with an RF burst containing information that was pre-programmed into the RFID tag.

Faraday cages are electrically conductive enclosures used to attenuate ("block") electromagnetic fields. They get their name from Michael Faraday, a British scientist from the 1800 s who established the conceptual basis for electromagnetic fields. Some of Faraday's work revealed the concept of electromagnetic shielding, which led to the Faraday cage.

Faraday cages are sometimes used to protect sensitive laboratory equipment from external electromagnetic interference (EMI). The laboratory equipment, for example, may be housed inside of a so-called "screen room" formed from a rigid frame covered with a conductive wire mesh. In use, signal leads may be passed through small holes in the mesh, into the interior of the screen room, and connected to the equipment. This allows the equipment to measure very small signals from a nearby experiment, signals that would otherwise be drowned out by environmental EMI.

Faraday bags are a type of Faraday cage made from flexible metallic fabric. The inventors are experts in the design of Faraday bags for holding wireless devices, or RFID tags, or both, in order to block inbound and outbound signals. Faraday bags have been incorporated into satchels, pouches, bags, handbags, briefcases, backpacks, and other accessories. In such case, the items are partially or completely formed from flexible metallic fabric. The result is enhanced digital privacy.

This application relates more specifically to modern freight tracking devices, another common emitter of RF signals that are intended for good, but can also do bad. The shipping industry is routinely using such tracking devices for logging and reporting locations and environmental conditions of the goods being shipped as they move from one place to another. They can track the assets over the road, in flight and even at sea.

FIGS. 1 and 2 show several typical freight tracking devices 11a to 11e that are made and sold by one of many manufacturers of such devices, here CalAmp Corp. They vary in size, capability, and re-usability. They are not shown actual size, but they are illustrated proportionally. The first freight tracking device 11a is a generally one-time use device that contains a battery and is irreversibly turned on when a break-off tab is removed (shown at the top right, but not separately numbered). The other freight tracking devices 11b to 11e also contain batteries, and related on/off switches of one kind or another, but they are intended to be recovered, restored or even repaired, and ultimately re-used.

It varies from make to maker, and model to model, but freight tracking devices generally monitor geographic location and environmental data. The location can be based on various location services (GPS, cellular triangularization, database lookups of known locations for WiFi access points, etc.). The environmental sensors can monitor things like temperature, humidity, light, shock, drops, orientation, vibration, etc. The devices can also be set so that the location and environmental data being tracked is checked at a desired rate, e.g. once per minute, once per hour, or once per day. The devices typically have onboard memory to log the data while the freight tracking device is offline, later reporting that data when the device comes in range of a reader or other communications channel such as an SC1000 device, Bluetooth LE reader, cell tower, WiFi access point, etc.

The logistics of recovering re-usable freight tracking devices is somewhat challenging. It requires workers on the receiving end to detach the tracking devices from the goods, pallets, or containers, and to mail them back to the manufacturer or some collection point within their own organization individually or in bulk.

Until the tracking devices are returned to the manufacturer, service provider, or other collection point, they are usually located in the warehouse or other receiving location. Unfortunately, while there, they generally continue transmitting RF signals that are of little value and, in fact, now constitute EMI. The Trojan horse from Greek mythology was welcomed into the city of Troy, and later Greek soldiers crept out of the horse and "interfered" with the city. In like fashion, the freight tracking devices that were attached to goods are welcomed into the warehouse, and the devices begin generating EMI. The inventors are informed that many modern warehouses contain other RF-based systems that are subject to significant degradation or failure in the presence of such EMI.

There remains a need, therefore, for a bag-in-a-box apparatus which uniquely incorporates a Faraday cage system and a self-closing, electromagnetically-attenuating device passage for recovering freight-tracking devices, temporarily storing the freight-tracking devices, substantially silencing the freight-tracking devices so they do not interfere with other sensitive equipment in the location where they are being recovered, and then enabling the convenient and electromagnetically-attenuated return of the freight-tracking devices for restoration and reuse.

There further remains a need for a container, soft- or hard-sided, that is normally RF-tight, but allows electronic devices to be inserted therein via a small passage or opening assembly and later removed as a group via a larger opening assembly.

SUMMARY OF THE INVENTION

The present invention provides structures and methods which overcome the deficiencies in the prior art.

In a first aspect, the invention resides in an apparatus for temporarily storing a plurality of electronic devices that transmit electromagnetic signals, comprising: a container that is sized for holding the plurality of electronic devices and adapted to be normally RF-tight to suppress the electromagnetic signals transmitted by the plurality of electronic devices to prevent the electronic devices from being accessed and from interfering with other electronic devices; a first small opening assembly in the container that opens and closes, the first small opening assembly being self-closing, the first small opening assembly adapted to allow insertion of an electronic device into the container when open, and to be RF-tight when closed such that the container returns to being RF-tight after insertion of the electronic device; and a second larger opening assembly in the container that opens and closes, the second larger opening assembly adapted to be RF-tight when closed, and to allow removal of the plurality of electronic devices as a group from the container when open.

In a second aspect, the invention resides in an apparatus for temporarily storing a plurality of shipping trackers, the shipping trackers being of a type used with shipped goods while the shipped goods are in transit from a first location to a second location, the shipping trackers usefully transmitting radio frequency (RF) transmissions containing data concerning a condition or location of the shipped goods while in transit but undesirably transmitting RF transmissions once the shipped goods have arrived at the second location due to potential inference with other devices at the second location, the apparatus suppressing the RF transmissions of the plurality of shipping trackers shortly after each shipping tracker arrives at the second location, and while the plurality of shipping trackers are stored as a group at the second location or elsewhere, comprising: a container that is adapted to be normally RF-tight and sized for holding the plurality of shipping trackers and adapted to suppress the RF transmissions from the plurality of shipping trackers to prevent interference with other electronic systems; a first small opening assembly in the container that opens and closes, the first small opening assembly adapted to allow insertion of a shipping tracker into the container when briefly open, and to be RF-tight when closed such that the container returns to being RF-tight when the first small opening assembly is closed; and a second larger opening assembly in the container that opens and closes, the second larger opening assembly adapted to be RF-tight when closed, and to allow for removal of the plurality of shipping trackers from the container as a group, when open, for refurbishment and re-use of the shipping trackers.

In a preferred embodiment, the apparatus container is a soft-sided warehouse bag that fits into and is secured inside of a cardboard shipping box that has an aperture that aligns with the first small opening assembly in the warehouse bag. This preferred embodiment is particularly suited to the need case of returning the electronic devices (shipping trackers) to a third-party logistics company. In other situations, however, the electronic devices may be removed from the container near to where they are initially deposited.

The apparatus, of course, may be implemented with a soft- or hard-sided container.

BRIEF DESCRIPTION OF THE DRAWINGS

FIG. 1 is a typical freight tracking device 11a that intended for one-time use;

FIG. 2 shows several other typical freight tracking devices 11b, 11c, 11d, and 11e that are intended for recovery and re-use;

FIG. 12 shows a cardboard box that is suitable for use with the preferred warehouse bag being chosen from several options;

DETAILED DESCRIPTION OF THE PREFERRED EMBODIMENTS

Figure 3:
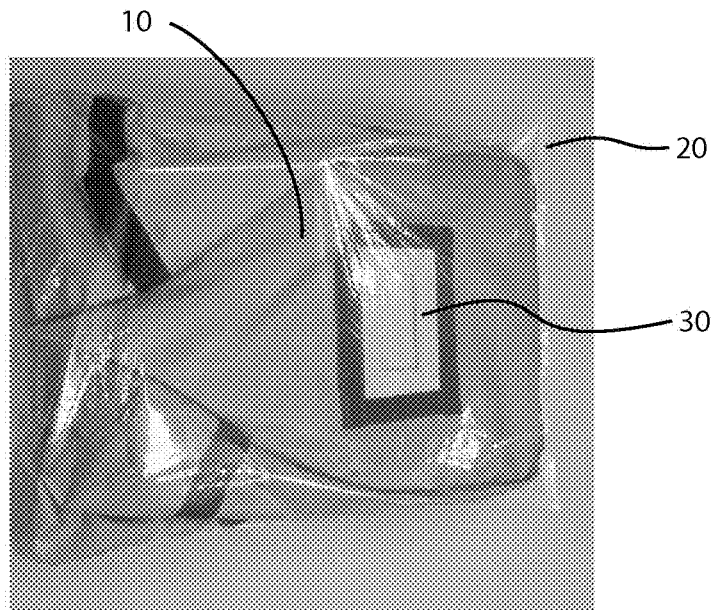
FIG. 3 shows a presently preferred Faraday bag 10, or "warehouse bag," in a plastic shipping bag 20 ready for delivery to a shipping logistics service provider for assembly into a storage/shipping box that is deployed in a customer warehouse that routinely receives freight tracking devices 11 that need to be returned to the logistics provider who owns the devices 11 and which, if not neutralized prior to return, may interfere with other RF communications in the warehouse.

The Faraday bag 10 disclosed herein was created to provide signal blocking protection (radio frequencies) to companies using Internet-of-Things (IOT) and other similar signal transmitting devices in the warehousing & transport industries—where the safekeeping of sensitive data and blocking of all wireless/Bluetooth/cellular/RFID signal is required for Radio Frequency (RF) interference purposes in transit and also when inside IOT connected warehouses.

Applicant's preferred embodiment of a warehouse bag 10 that can be combined into a cardboard box 40 to form a storage/shipping box 100 is best understood with reference to the figures and following description.

The preferred warehouse bag 10 is formed from the following fabric or fabric-like materials, combined with Velcro® strips for securement to a suitably sized and apertured box 40:

External: One layer of 100% rip-stop nylon; and
Internal: three layers of shielding material, e.g. 58% polyester/28% copper/14% nickel The warehouse bag 10 also features a unique trapdoor 30 and a large, roll-down top that are designed to maintain an RF tight enclosure.

How it Works

1. The Faraday bag 10 comes equipped with external sewn-on mounting strips (the loop- or fuzzy-side of Velcro®) that are easily secured to mating strips (the hook-side of Velcro®) adhered to the inside of a standard cardboard shipping box, preferably to the bottom of the box and also to the side where an opening is cut to align with the bag's trapdoor 30.

2. The Faraday bag's top roll-down opening is rolled down three times and firmly held in a closed, and then rolled-down position by two pairs of mating Velcro® strips to ensure signal blocking protection. The large opening is sealed by one pair of Velcro® strips with the inside shielding material on opposing panels in contact with one another, and then the top of the bag is rolled over and held in the roll-over configuration with the other pair of Velcro® strips to maintain the conductive contact that block signal.

3. The Faraday bag 10 is then placed into a cardboard shipping box 40 that has a small cut out hole (or flap) that aligns to the magnetic trapdoor 30 of the Faraday bag 10. This hole (or flap) is manually cut into the box and is relatively small so it can be easily sealed up when the box/bag combo is full and ready for shipment.

4. Warehouse workers are then able to easily drop in large quantities (30+) signal transmitting IOT's 11 (connected through Bluetooth, GPS and cellular) into the box/bag combo 100 formed from faraday bag 10 and the box 40, through the magnetic trapdoor 30—secure the hold (or flap) in the cardboard box 40, and return the devices 11 securely, ensuring no signal or data is leaked, transmitted or scanned while in transit. And further the devices 11 are not sending out interfering RF signals while stored in the bag 10 inside the warehouse.

5. The large roll-down Velcro® opening and closure system allows for efficient removal of the devices 11 at the final destination, i.e. for recycling, refurbishments, or repurposing.

The Presently Preferred Embodiment

FIGS. 1 and 2 show some typical freight tracking devices 11, including one small, low cost device 11a that is intended for one-time use and several other more expensive freight tracking devices 11b, 11c, 11d, and 11e that are relatively expensive and are intended for recovery, restoration, and re-use. These devices form part of the IOT environment.

The illustrated warehouse bag 10 is a Faraday bag that is specifically designed for receiving, holding, and shipping IOT devices like the freight tracking devices 11. It is suitable for any device that connects to a cellular, GPS, Bluetooth, Wireless, WiFi, or RFID signal.

The warehouse bag 10 is designed to fit into a standard cardboard box 40, e.g. a Uline box, that is easily retrofitted to allow devices to be received in the bag 10, where they can remain until ready to return while simultaneously blocking signal.

This allows the user, or company, to know that all private information or data is completely blocked from the outside world, and to prevent the stored devices from interfering with other communication channels, until it is time to open the box 40 and bag 10 from the top.

As shown, the preferred warehouse bag 10 is designed for functionality and ease of use. It features a magnetic self-closing trapdoor 30, a Velcro® top seal that operates on a roll-down basis, Velcro® connection to the side of the cardboard box in the area of the trapdoor 30, and Velcro® connection to the bottom of the cardboard box.

Figure 4:
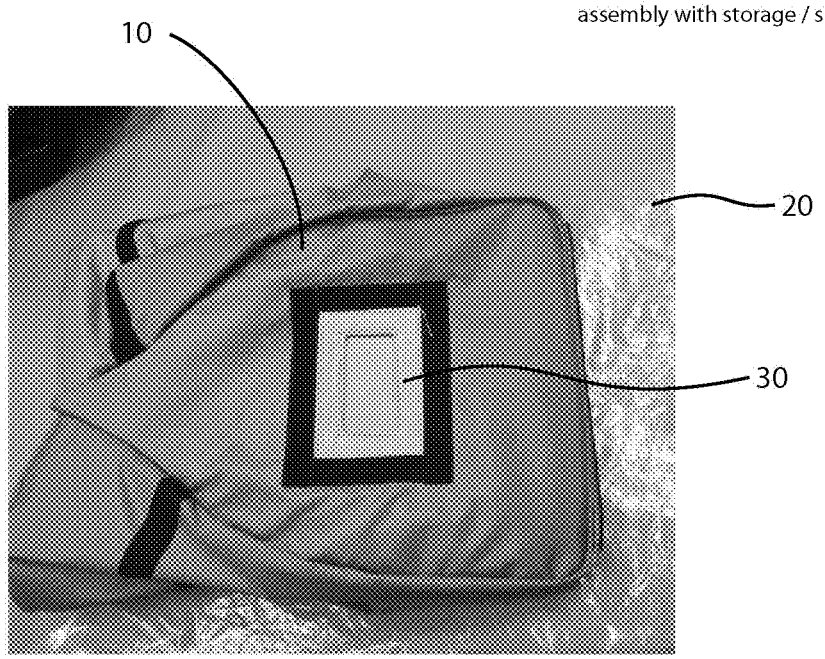
FIG. 4 shows the warehouse bag 10 removed from the plastic bag 20.
Figure 5:
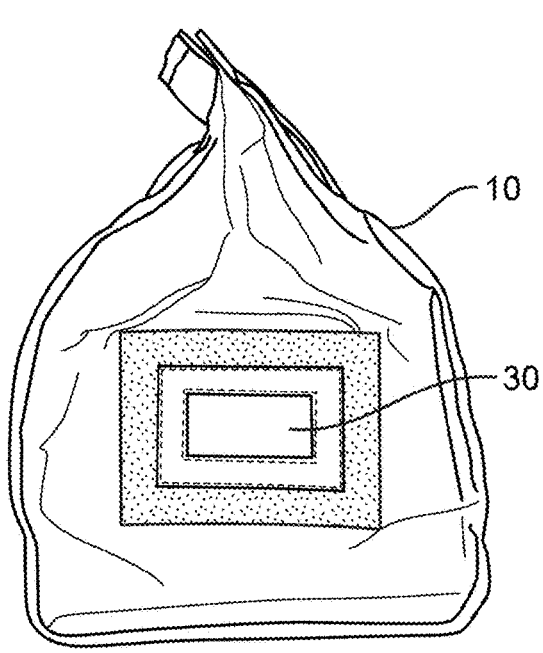
FIG. 5 shows a first end of the warehouse bag 10, now expanded, which features a trap door 30.
Figure 6:
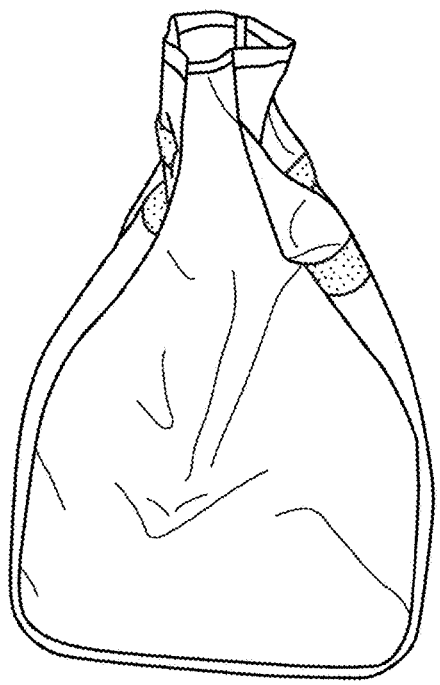
FIG. 6 shows an opposite end of the warehouse bag 10.
Figure 7:
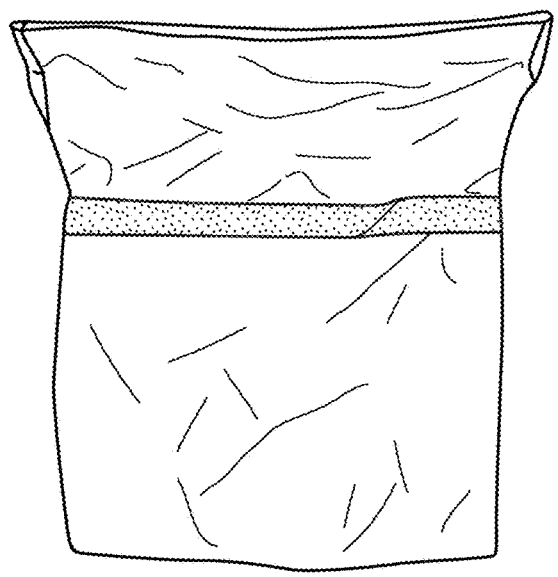
FIG. 7 shows the roll-toward side of the warehouse bag 10, now expanded, with the rolltop still open.
Figure 8:
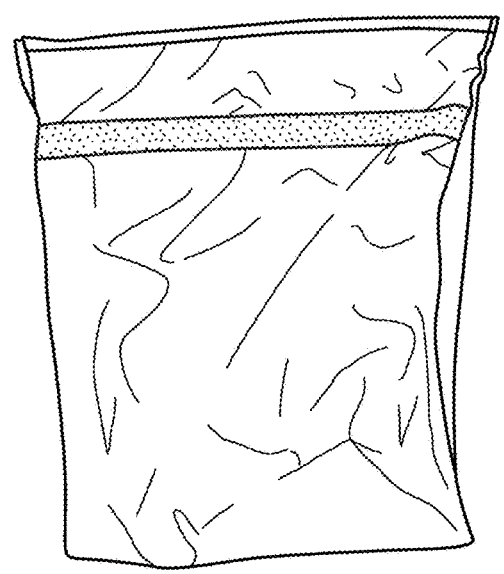
FIG. 8 shows the roll-from side of the warehouse bag 10, now expanded, with the rolltop still open.
Figure 9:
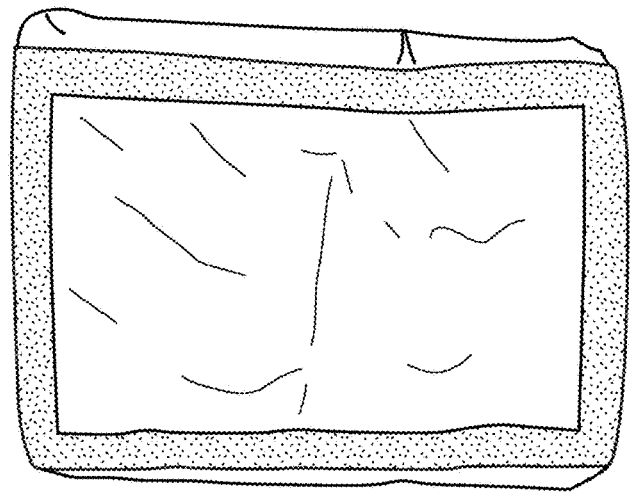
FIG. 9 shows the bottom of the warehouse bag 10 with Velcro® strips for securing the bag in a storage/shipping box.
Figures 10, 11:
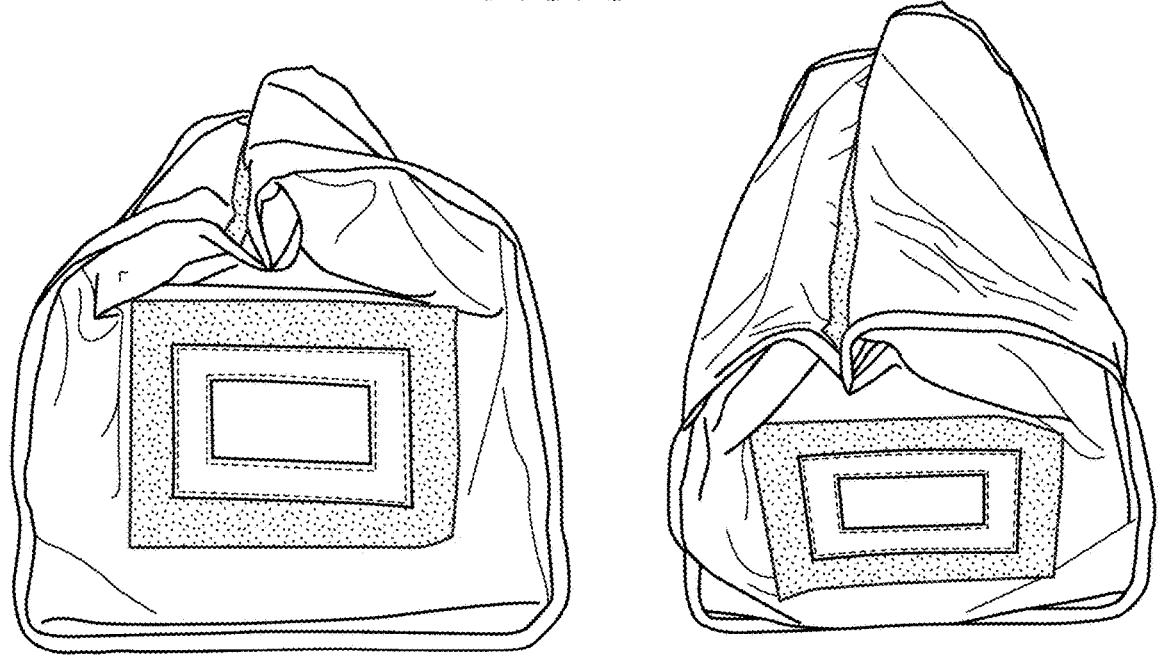
FIG. 10 shows the trapdoor end of the warehouse bag 10 with the rolltop closed.
FIG. 11 also shows the trapdoor end of the warehouse bag 10 with the rolltop closed, but from a higher viewpoint.

FIGS. 3 and 4 show a presently preferred Faraday bag 10, or "warehouse bag," in a plastic shipping bag 20 ready for delivery to a shipping logistics service provider for assembly into a storage/shipping box that is deployed in a customer warehouse that routinely receives freight tracking devices 11 that need to be returned to the logistics provider who owns the devices 11 and which, if not neutralized prior to return, may interfere with other RF communications in the warehouse;

FIGS. 5 to 11 shows the warehouse bag 10 from various sides, revealing the preferred location of the trapdoor 30, the Velcro® strips, etc.

Figure 12:
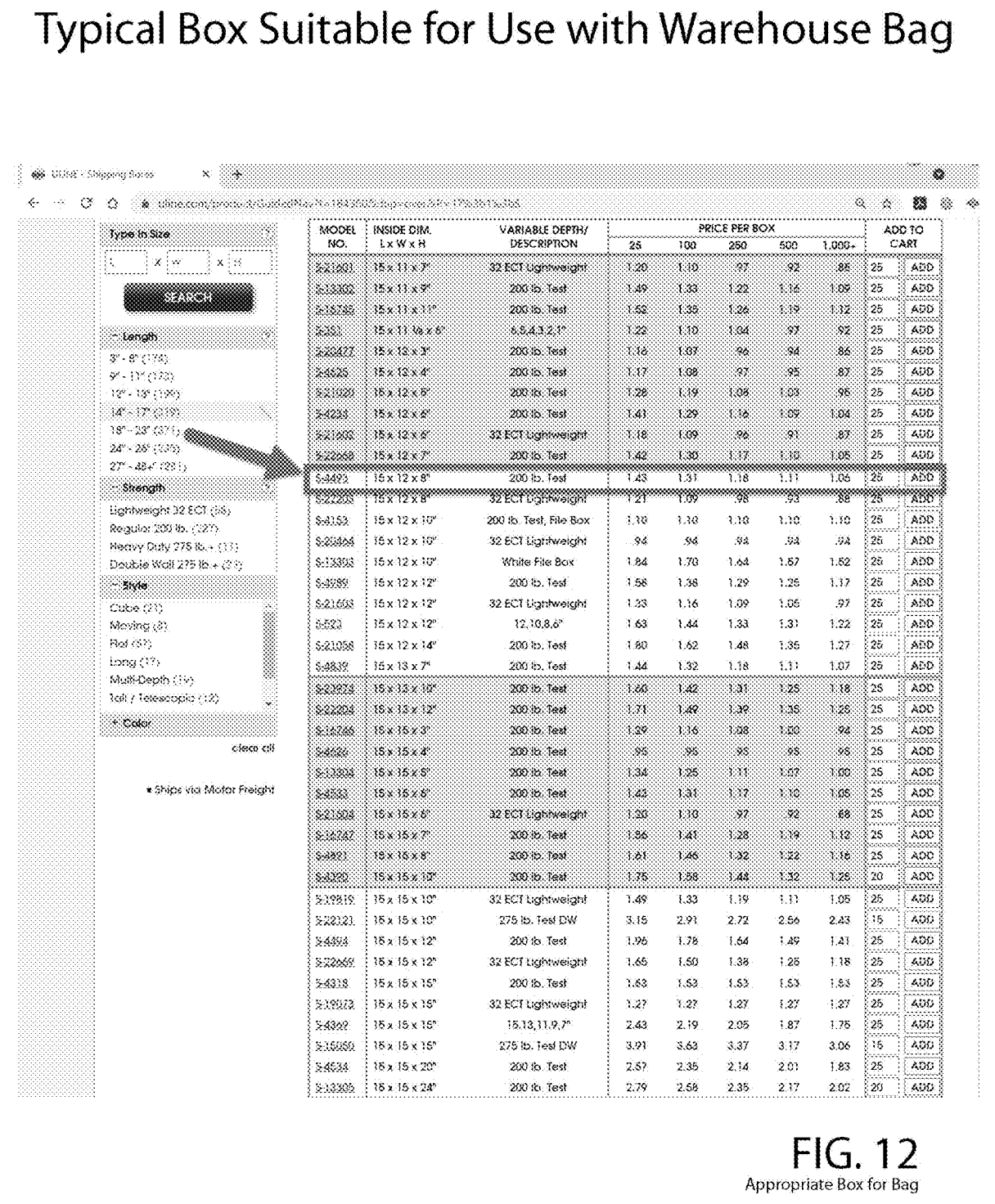
Figure 13:
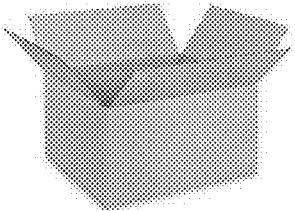
FIG. 13 shows the cardboard box that is suitable for use with the preferred warehouse bag 30.

FIGS. 12 and 13 show the selection of a suitably dimensioned cardboard box, here 15"×12"×8". The presently preferred warehouse bag 10 is 17"H×14" L×11.5" D, so the deformable bag will fit tightly within the box 40.

Assembly

Figure 14:
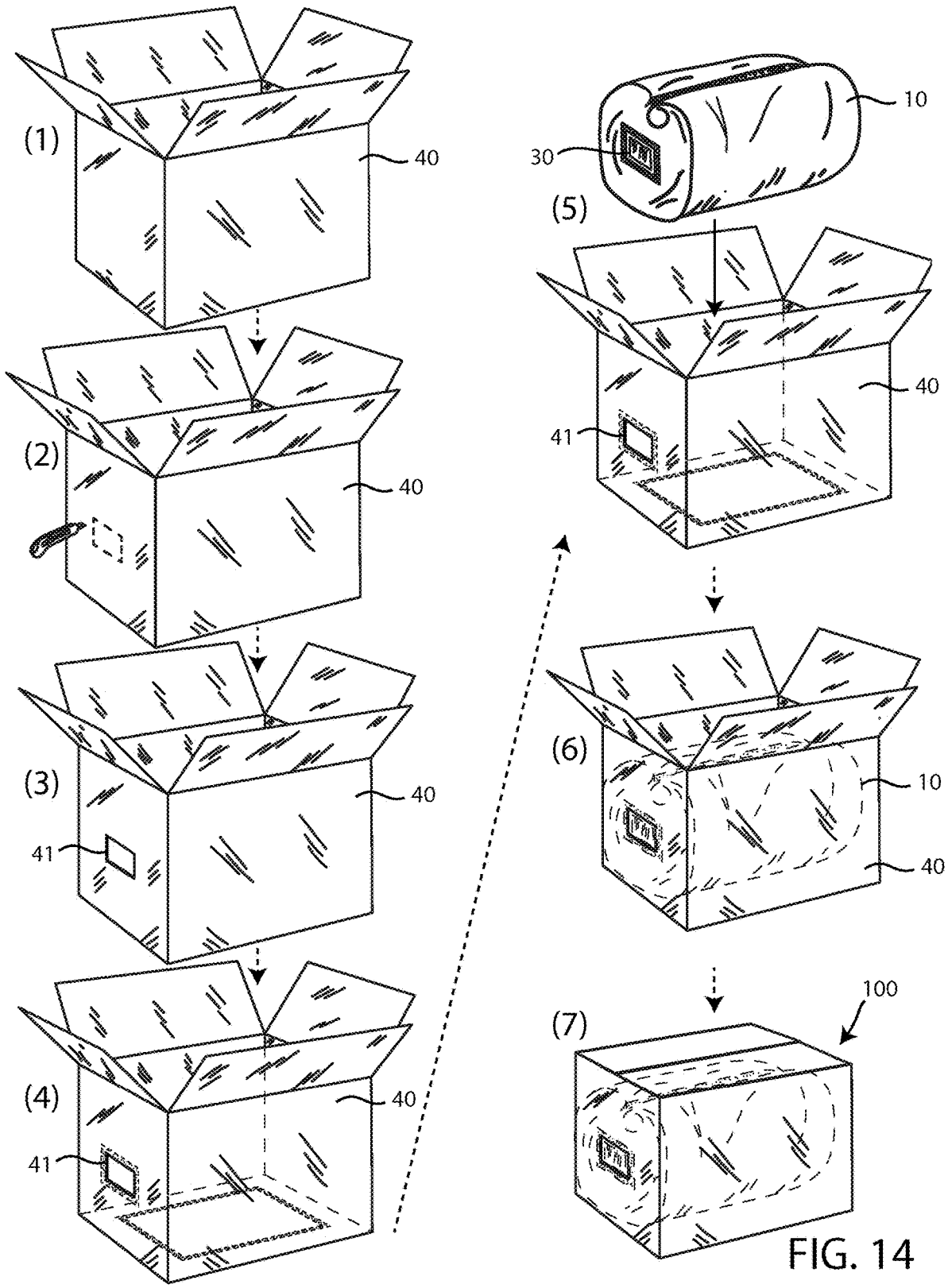
FIG. 14 is a series of illustrations showing how a cardboard box 40 is modified to have an open four-sided window and then outfitted with a warehouse bag 10 that has its trapdoor aligned with the window to form an RF-tight storage/shipping box 100.
Figure 15:
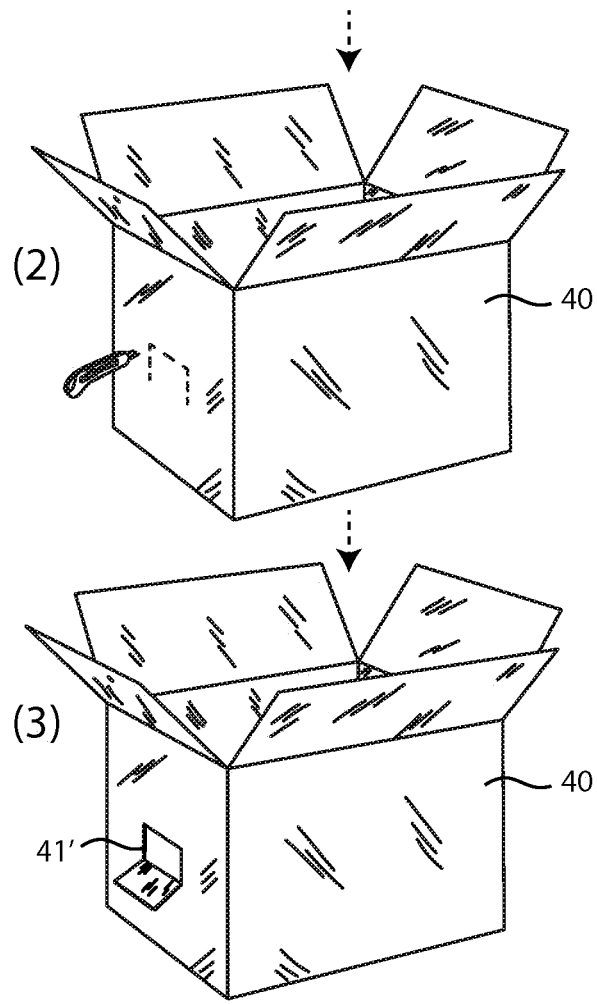
FIG. 15 shows an alternative approach to modifying the cardboard box 40 by cutting out a three-sided flap rather than a four-sided window.

FIG. 14 is a series of illustrations showing a presently preferred assembly process where a cardboard box 40 is modified to have an open four-sided window 41 that is located so the warehouse bag's trapdoor 30 aligns with the opening when the bag 10 is dropped into the box 40, thereby forming an easily accessed, RF-tight storage/shipping box 100;

FIG. 15 shows an alternative approach to modifying the cardboard box 40 by cutting out a three-sided flap 41' rather than a four-sided window 41;

Use

In use, the RF-tight storage/shipping box 100 is simply located in a convenient location for warehouse workers to drop in tracking devices 11 after removing them from goods or pallets containing goods. A possible scenario, for example, is locating the RF-tight storage/shipping box 100 on a rolling table in the loading dock area of a warehouse.

Figure 16:
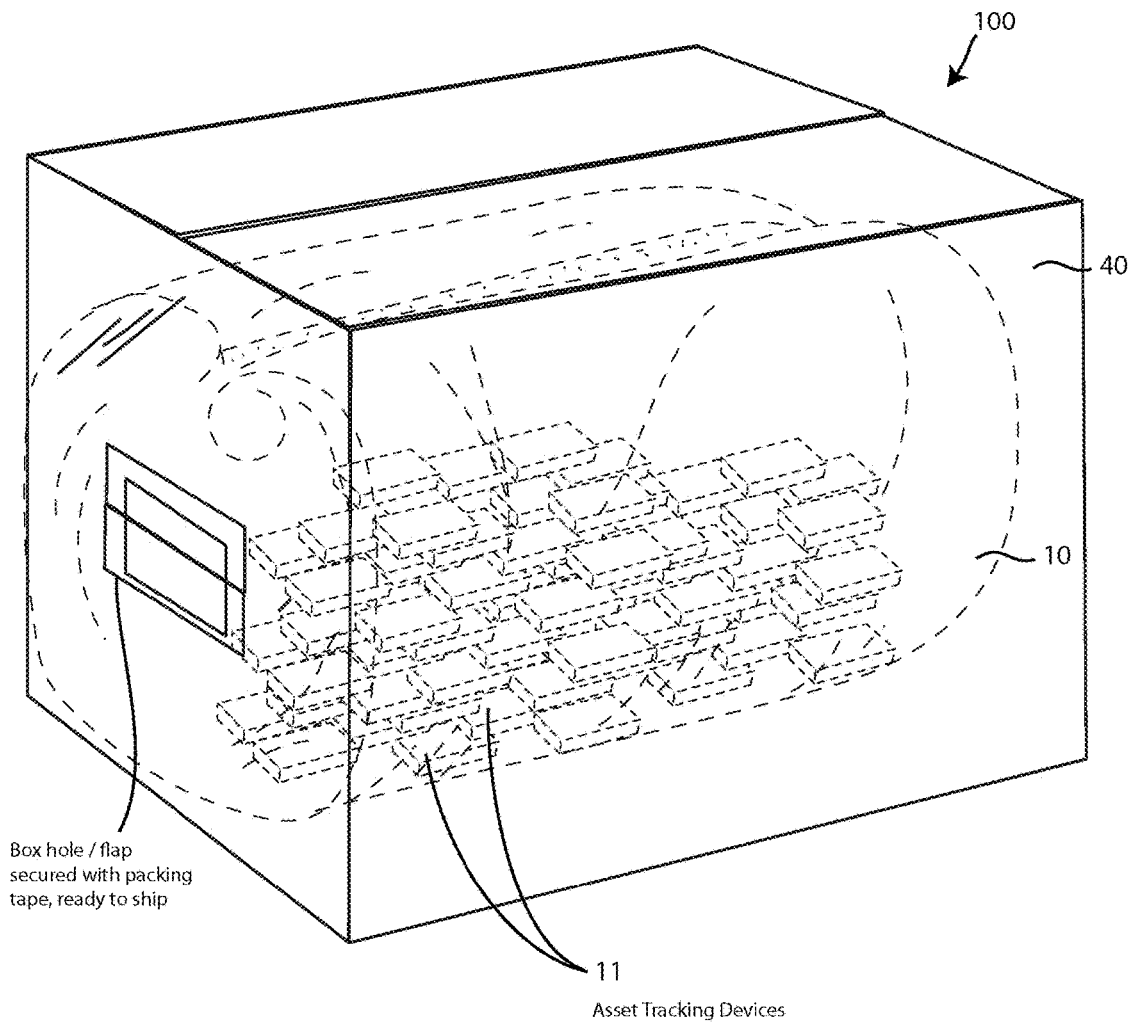
FIG. 16 shows a shipping/storage box 100 that is full of asset tracking devices 11 and now read to be returned to the logistics provider.

Eventually, the box will fill up and be ready for return. FIG. 16 shows a shipping/storage box 100 that is full of asset tracking devices 11 and now read to be returned to the logistics provider. The warehouse bag 10 could, of course, be used to store and transport multiple cell phone (e.g. 20) or other electronic device without connection.

Preferred Construction

Figure 17:
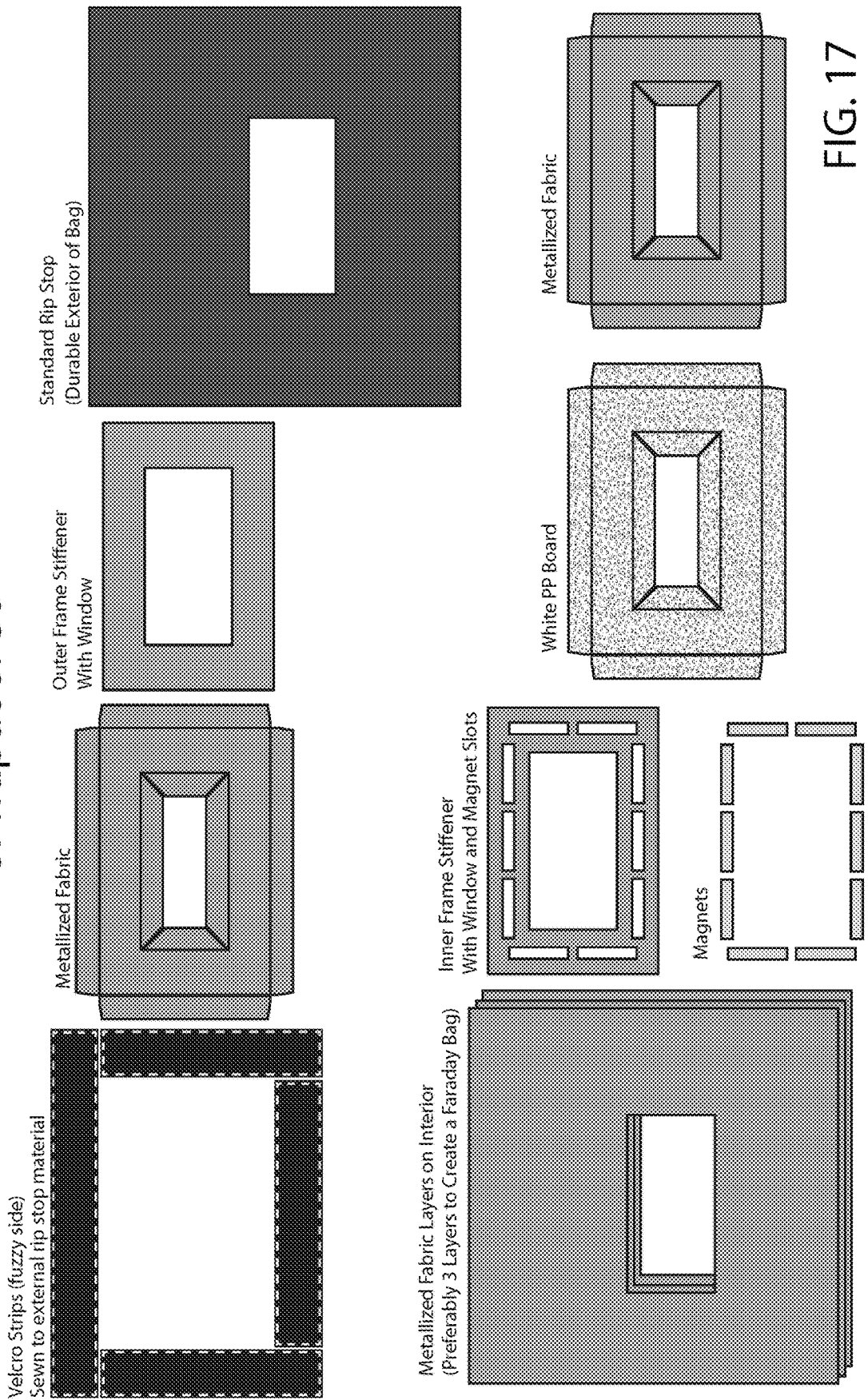
FIG. 17 is an exploded view of the components that are assembled into the magnetic frame that forms one half of the presently preferred trap door 30.
Figure 18:
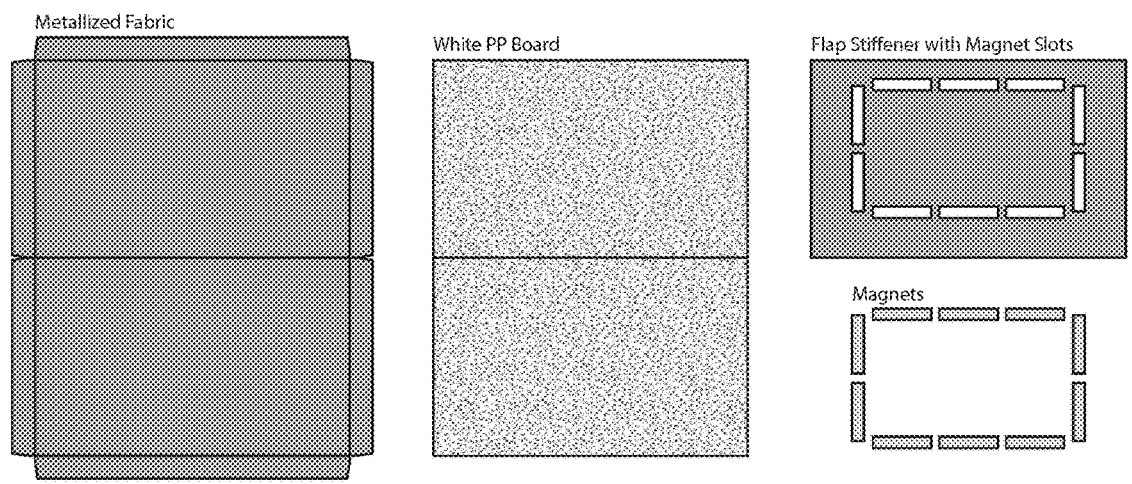
FIG. 18 is an exploded view of the components that are assembled into the magnetic flap that forms the other half of the presently preferred trap door 30.

As noted above, the preferred warehouse bag 10 is formed from the following fabric or fabric-like materials, combined with Velcro® strips for securement to a suitably sized and apertured box 40:

External: One layer of 100% rip-stop nylon; and
Internal Lining: three layers of Multishield™ shielding material, e.g. 58% polyester/28% copper/14% nickel
The presently preferred trapdoor 30 is formed from
450 gm paper
one layer of 0.8 mm PP board
three layers of Multishield™ Faraday lining signal blocking shielding material
20 small magnets, 10 in the frame and 10 in the flap;
several strips of Velcro FIGS. 17 and 18 are exploded views of the above-listed components that are assembled into the magnetic frame that forms one half of the presently preferred trap door 30 and magnetic flap that forms the other half of the presently preferred trap door 30. As shown, an arrangement of magnets on the frame and flap allow the trapdoor 30 to be pushed open, but then automatically closes due to gravity in combination with the magnets to pull it closed and keep it firmly closed for RF-tightness.

The presently preferred Faraday bag 10 features a self-closing RF-tight device passage for recovering, temporarily storing, and then returning freight-tracking transmitters. The preferred device passage is a trapdoor 30 that is configured as a top-hinged flap that closes due to gravity and integrated magnets, but there are many possible configurations in terms of shape and closure biases, including an overlapping slit-like arrangement of fabric, and closure biases provided by other elements such as springs, living hinges, etc.

Figure 19:
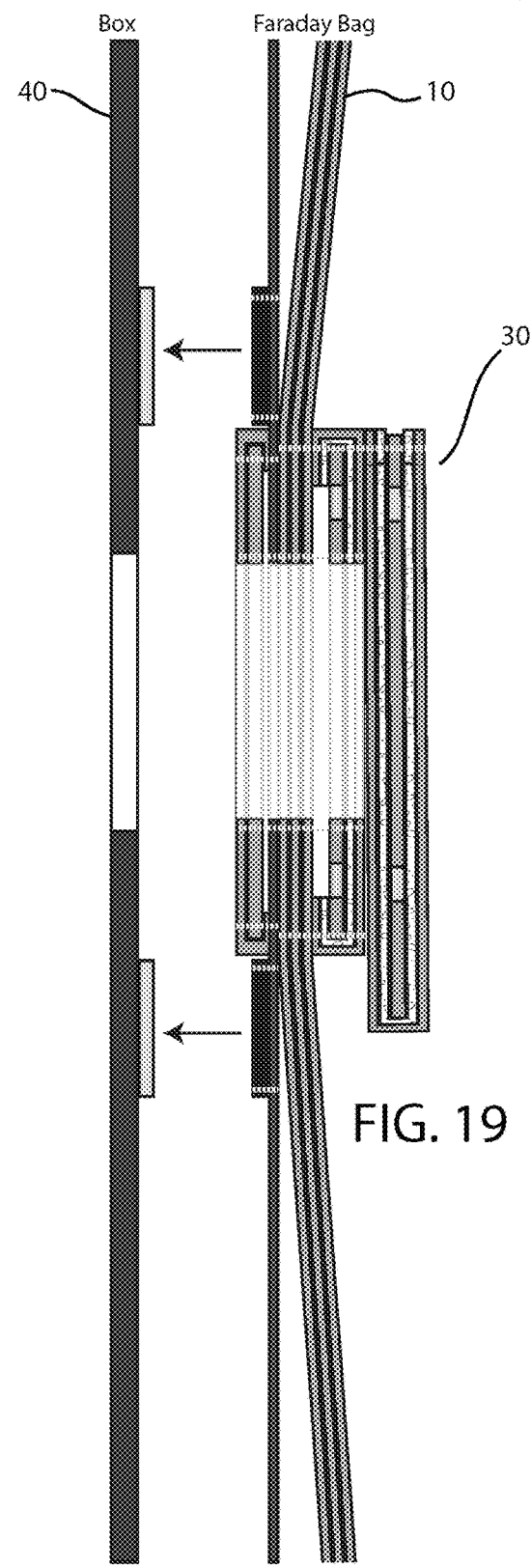
FIGS. 19 to 20 show the detailed construction of the presently preferred trapdoor 30 of the warehouse bag 10, and it being secured to the window in the box 40 with Velcro® to form the RF-tight storage/shipping box 100 shown in FIGS. 14 and 16.
Figure 20:
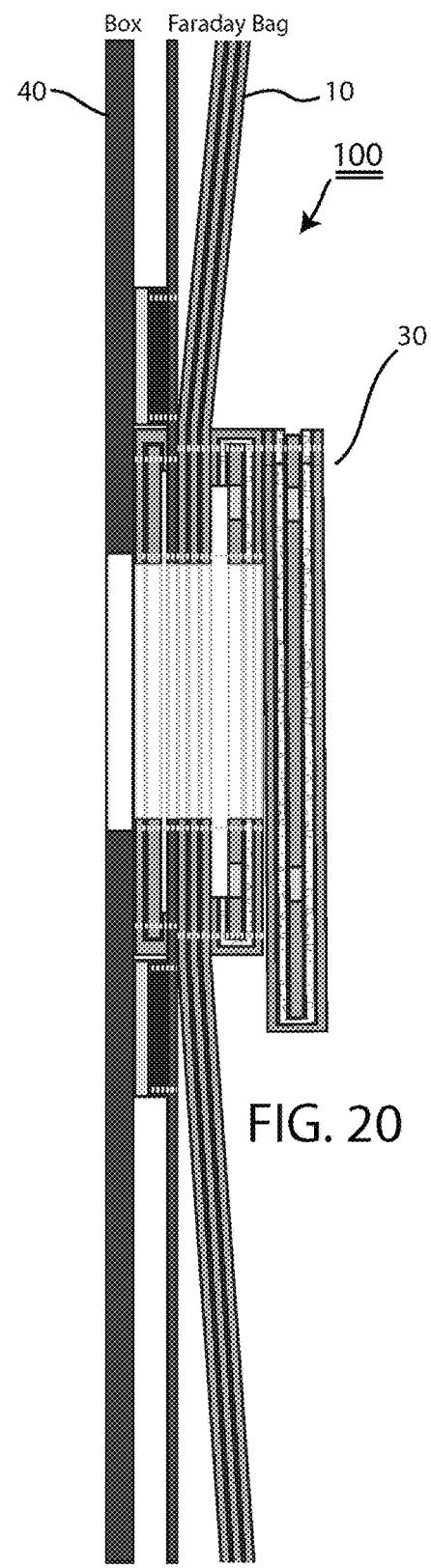

FIGS. 19 to 20 are cross-sectional sides views that show the detailed construction of the presently preferred trapdoor 30 of the warehouse bag 10, and it being secured to the window in the box 40 with Velcro® to form the RF-tight storage/shipping box 100 shown in FIGS. 14 and 16. The dashed lines represent the presently preferred stitching that generally provides for a robust assembly that further allows for a continuously conductive connection in the trapdoor region when the trapdoor 30 is closed.

Figure 21:
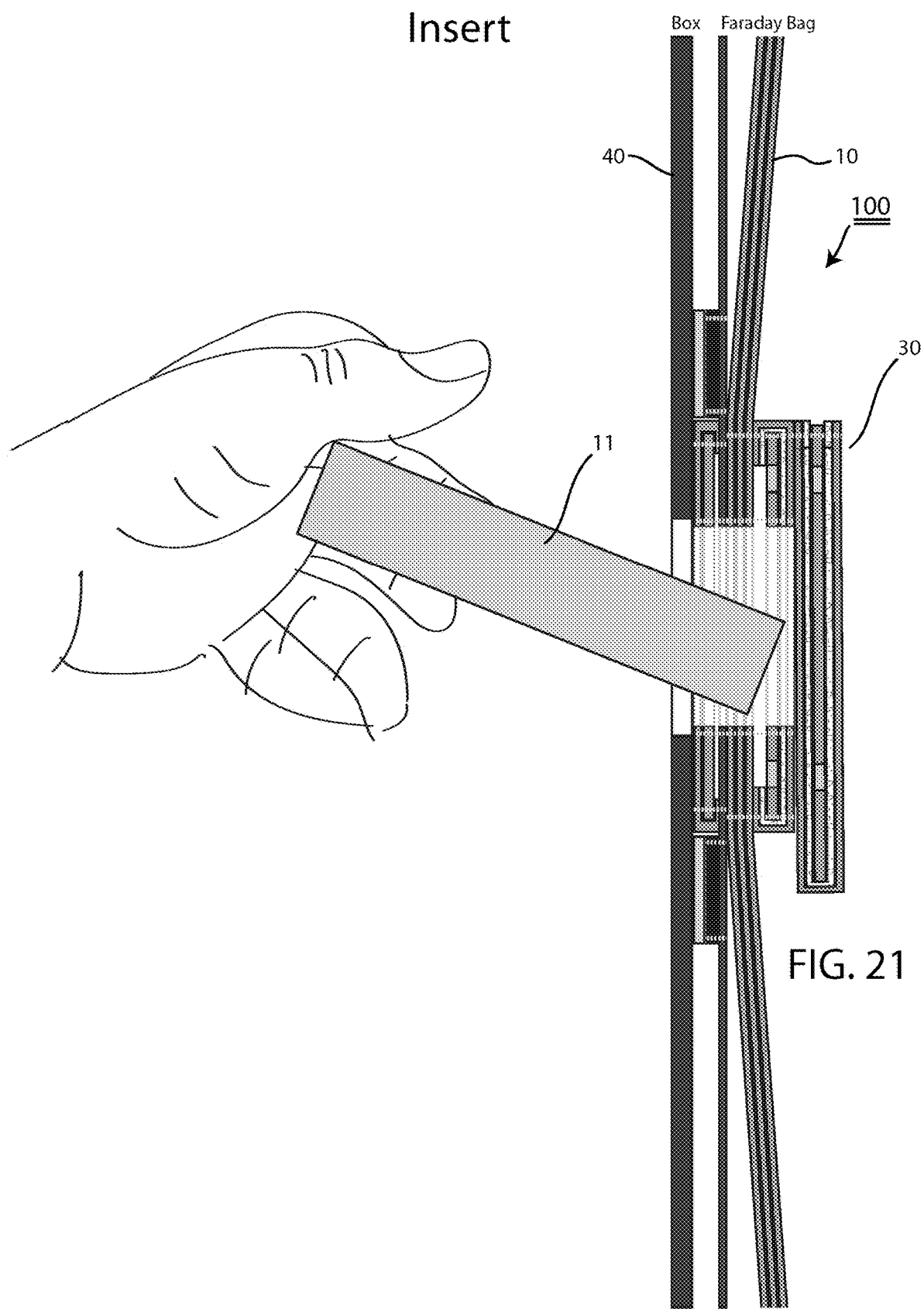
FIGS. 21 to 23 show an asset tracking device 11 being inserted through the trap door 30, past the magnetic closing forces, and then dropped into the storage/shipping box 100.
Figure 22:
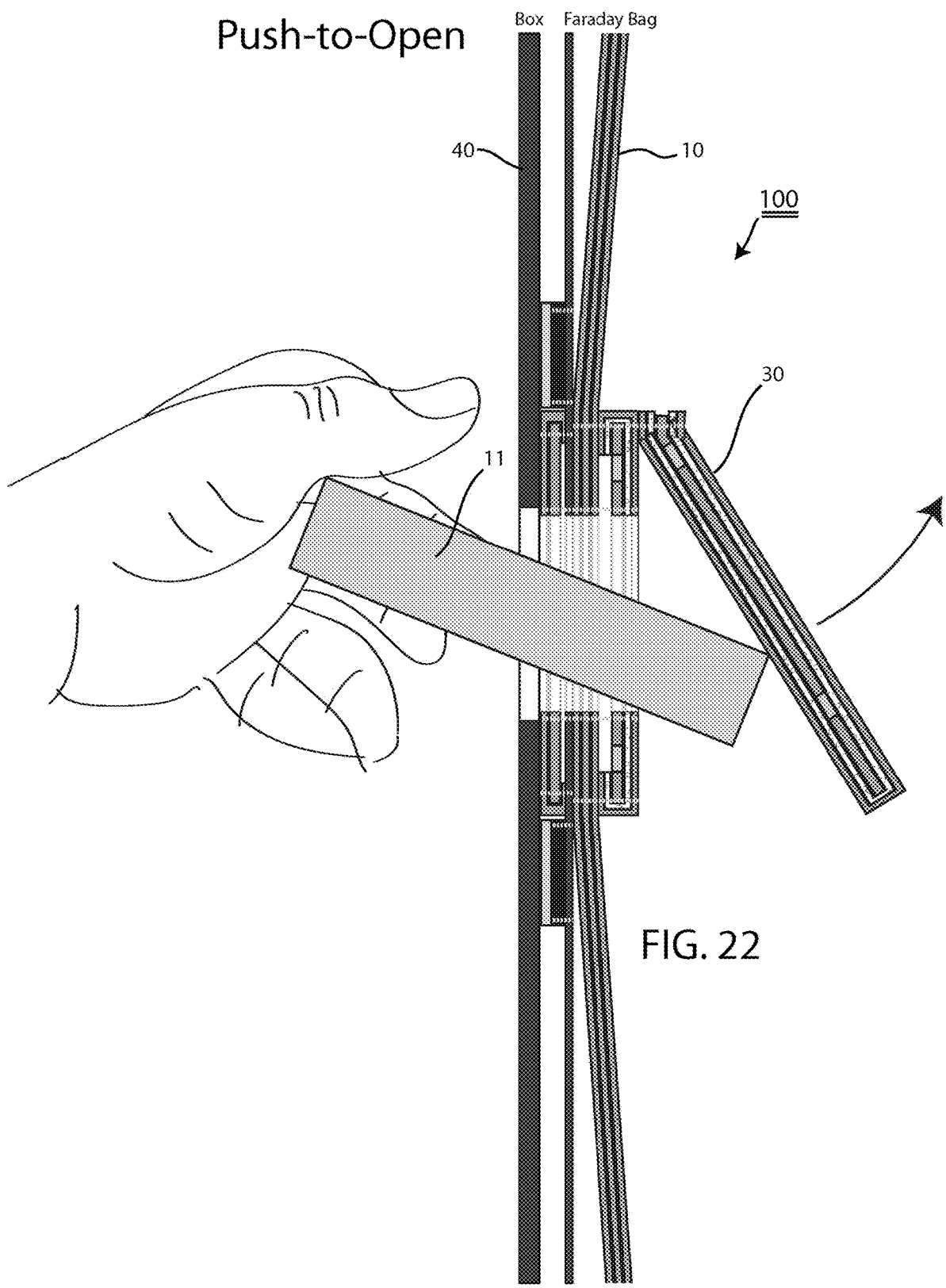
Figure 23:
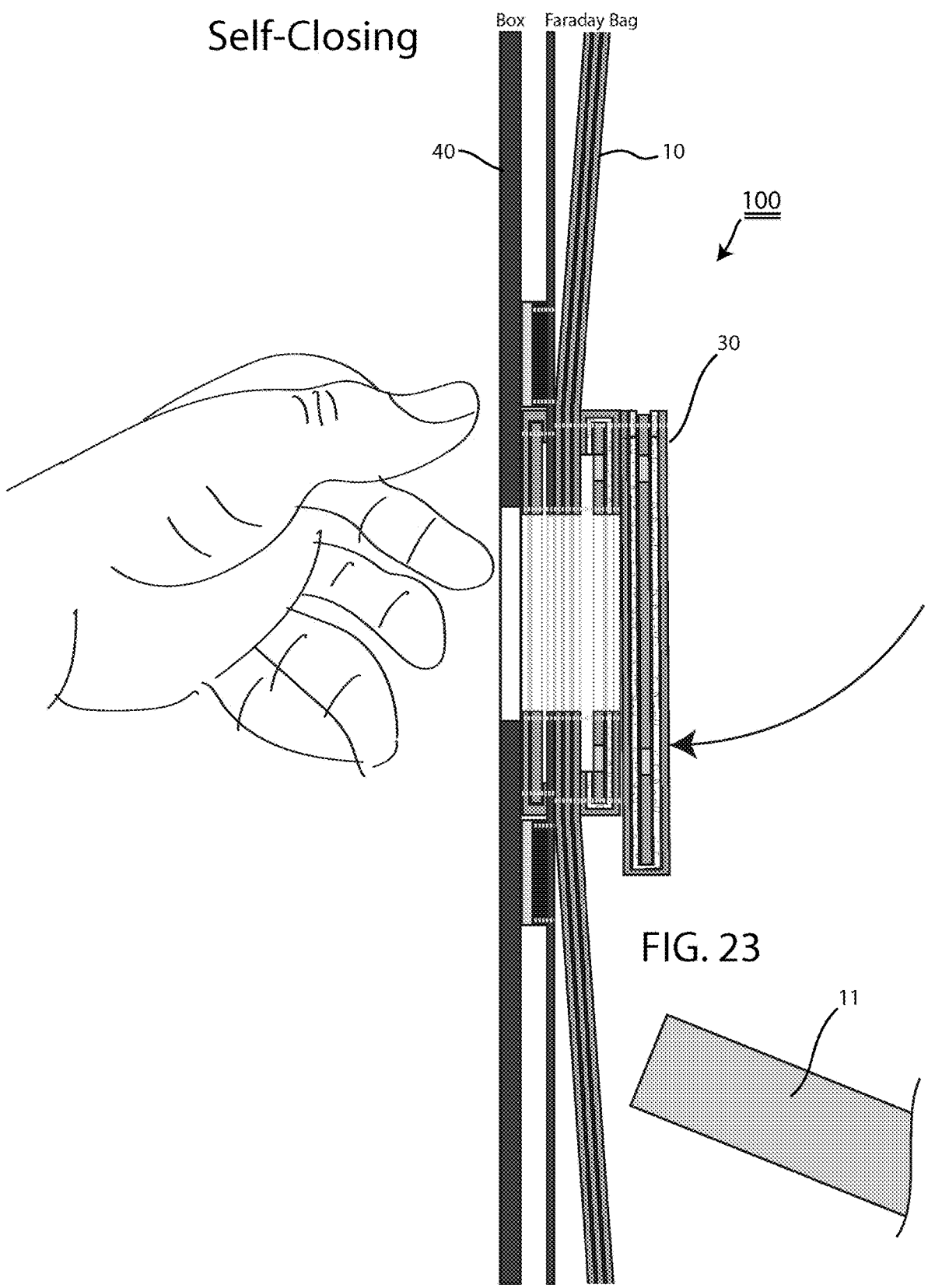
Figure 24:
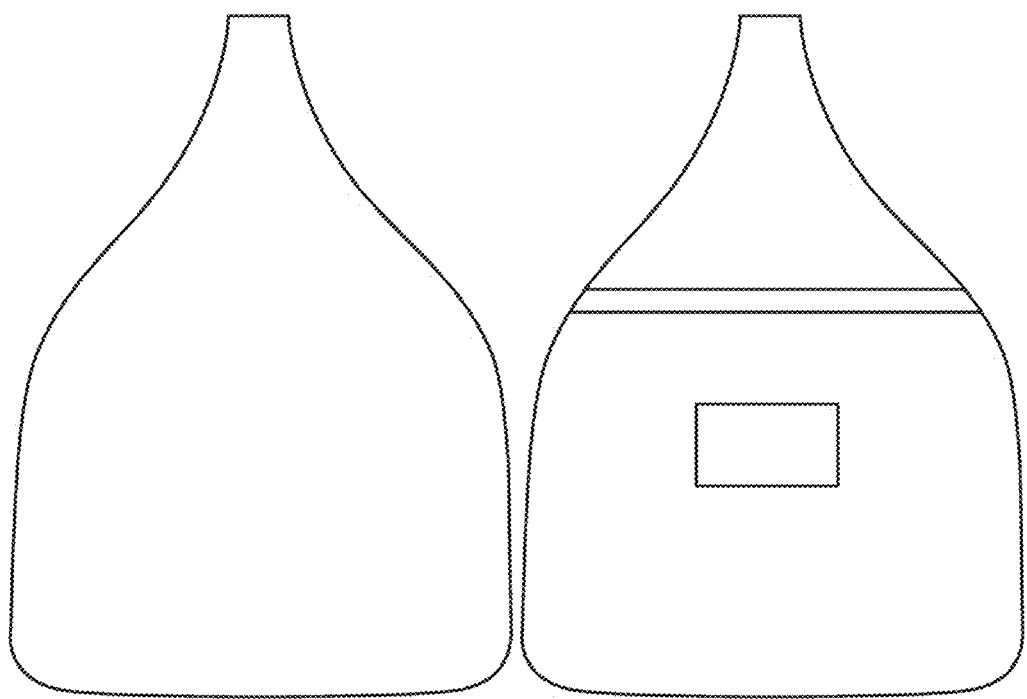
FIGS. 24 to 27 show the cutting patterns used to mark and cut the layers of special fabric and other components that are stitched and glued together in order to make the presently preferred Faraday bag 30.
Figure 25:
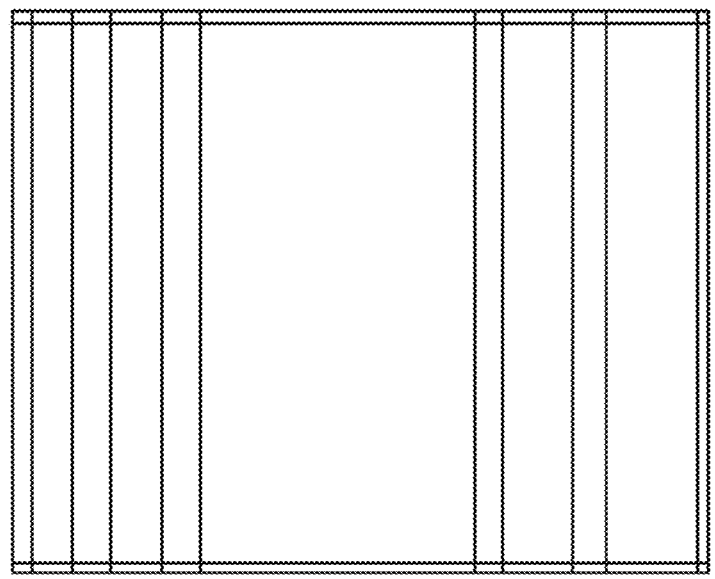
Figure 26:
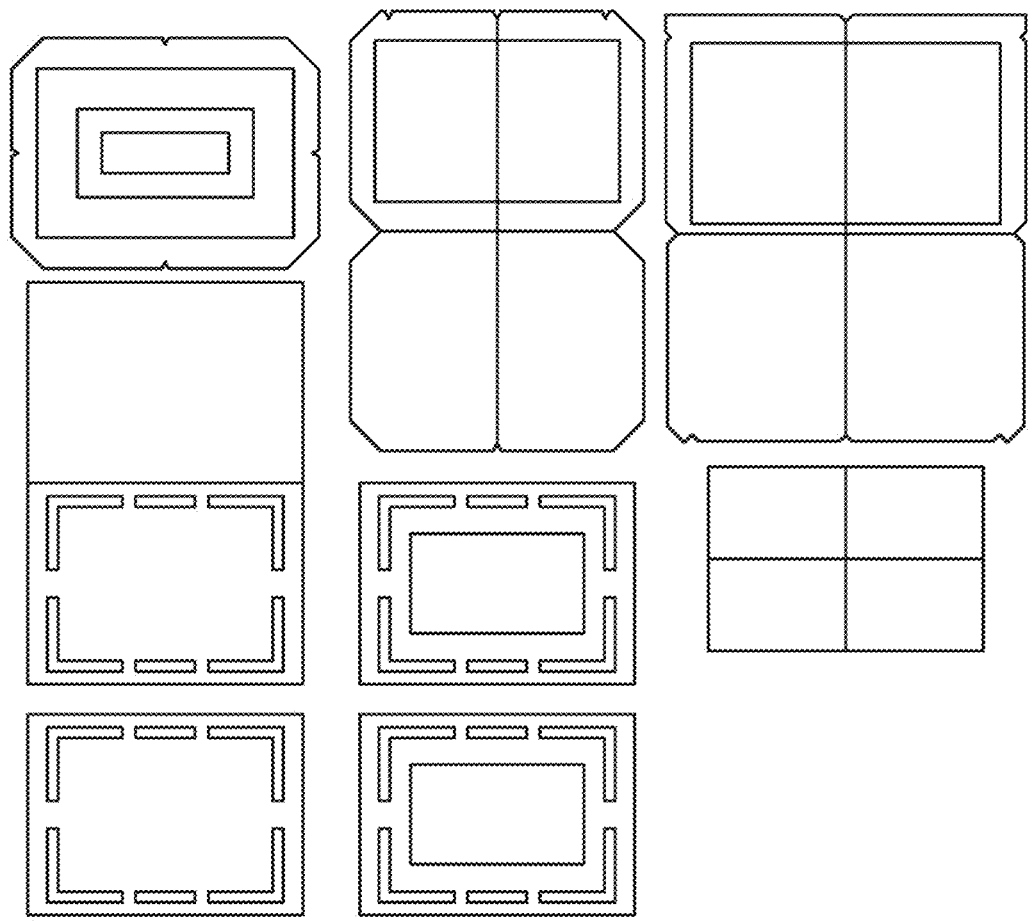
Figure 27:

FIGS. 21 to 23 show an asset tracking device 11 being inserted through the trap door 30, past the magnetic closing forces between the magnets in the frame and flap, and then dropped into the storage/shipping box 100.

FIGS. 24 to 27 show the cutting patterns used to mark and cut the layers of special fabric and other components that are stitched and glued together in order to make the presently preferred Faraday bag 30.

Figure 28:
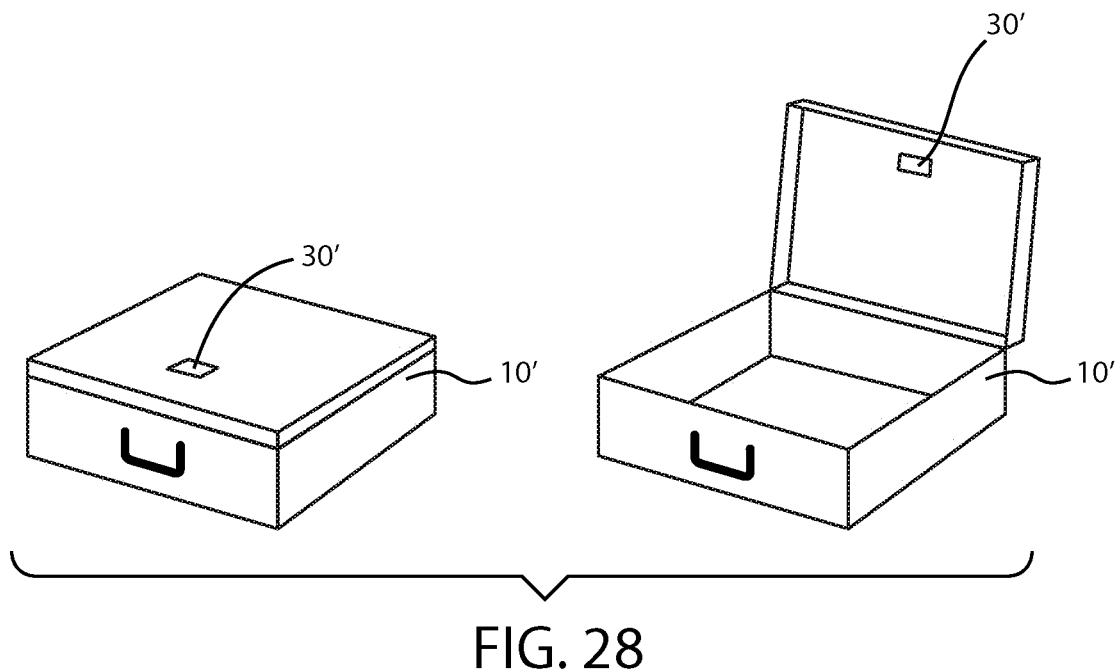
FIG. 28 shows an alternative embodiment that uses a hard-side container 10' instead of a soft-sided bag 10, the hard-sided container 10' being equipped with a suitable trap door 30'.

FIG. 28 shows an alternative embodiment that uses a hard-sided container 10' instead of a soft-sided bag 10, the hard-sided container 10' being equipped with a suitable flap 30'. As should be apparent, the hard-sided container could be formed from a case like those sold under the Pelican® brand, which has been modified to be RF-tight and equipped with a suitable flap or trap door 30' that allows for the insertion of a shipping tracker or other electronic device.

In order to even more effectively block electronic signals, the inventors contemplate that the warehouse bag 10's trapdoor 30 area may later feature the parallel rib structures that were incorporated into the security pouch disclosed in U.S. Pat. No. 9,460,309.

The invention claimed is:

1. An apparatus for temporarily storing a plurality of electronic devices that transmit electromagnetic signals, comprising:
   a container that is sized for holding the plurality of electronic devices and adapted to be normally RF-tight to suppress the electromagnetic signals transmitted by the plurality of electronic devices to prevent the electronic devices from being accessed and from interfering with other electronic devices;
   a first small opening assembly in the container that opens and closes, the first small opening assembly being self-closing, the first small opening assembly adapted to allow insertion of an electronic device into the container when open, and to be RF-tight when closed such that the container returns to being RF-tight after insertion of the electronic device; and
   a second larger opening assembly in the container that opens and closes, the second larger opening assembly adapted to be RF-tight when closed, and to allow removal of the plurality of electronic devices as a group from the container when open.

2. The apparatus of claim 1 wherein the first small opening assembly comprises a hinged flap that is hinged at the top whereby gravity tends to close the hinged flap.

3. The apparatus of claim 2 wherein the first small opening assembly further comprises:
   a frame supporting the hinged flap;
   a magnet on the frame; and
   a magnet on the flap that is attracted to the magnet on the frame to keep the flap firmly closed against the frame.

4. The apparatus of claim 1 further comprising:
   a cardboard shipping box sized to receive the container; and
   an opening in a side of the cardboard shipping box positioned in alignment with the first small opening assembly in the container.

5. The apparatus of claim 4 further comprising:
   a first set of hook or loop fastening material located on an exterior of the container adjacent to the first small opening assembly; and
   a second set of hook or loop fastening material located on an interior of the cardboard shipping box and adjacent to the opening such that the first small opening assembly is mechanically held next to the opening in the carboard shipping box.

6. The apparatus of claim 4 wherein the opening in the side of the cardboard shipping box is formed from a three-sided flap cut into the cardboard shipping box.

7. The apparatus of claim 1 wherein the container is a soft-sided container.

8. The apparatus of claim 7 wherein the soft-sided container is a bag.

9. The apparatus of claim 8 wherein the second larger opening assembly comprises a roll-down opening.

10. The apparatus of claim 9 wherein the roll-down opening is held closed with hook and loop fasteners.

11. The apparatus of claim 1 wherein the container is a hard-sided container.

12. The apparatus of claim 11 wherein the hard-sided container is comprised of a hard case with a bottom and a top and wherein the second larger opening assembly is comprised of the opening formed when the top is rotated away from the bottom.

13. The apparatus of claim 12 wherein the first small opening assembly is separate from the second larger opening assembly.

14. An apparatus for temporarily storing a plurality of shipping trackers, the shipping trackers being of a type used with shipped goods while the shipped goods are in transit from a first location to a second location, the shipping trackers usefully transmitting radio frequency (RF) transmissions containing data concerning a condition or location of the shipped goods while in transit but undesirably transmitting RF transmissions once the shipped goods have arrived at the second location due to potential inference with other devices at the second location, the apparatus suppressing the RF transmissions of the plurality of shipping trackers shortly after each shipping tracker arrives at the second location, and while the plurality of shipping trackers are stored as a group at the second location or elsewhere, comprising:
a container that is adapted to be normally RF-tight and sized for holding the plurality of shipping trackers and adapted to suppress the RF transmissions from the plurality of shipping trackers to prevent interference with other electronic systems;
a first small opening assembly in the container that opens and closes, the first small opening assembly adapted to allow insertion of a shipping tracker into the container when briefly open, and to be RF-tight when closed such that the container returns to being RF-tight when the first small opening assembly is closed; and
a second larger opening assembly in the container that opens and closes, the second larger opening assembly adapted to be RF-tight when closed, and to allow for removal of the plurality of shipping trackers from the container as a group, when open, for refurbishment and re-use of the shipping trackers.

15. The apparatus of claim 14 wherein the first small opening assembly is self-closing.

16. The apparatus of claim 15 wherein the first small opening assembly comprises a hinged flap that is hinged at the top whereby gravity tends to close the hinged flap.

17. The apparatus of claim 16 wherein the first small opening assembly further comprises:
a frame supporting the hinged flap;
a magnet on the frame; and
a magnet on the flap that is attracted to the magnet on the frame to keep the flap firmly closed against the frame.

18. The apparatus of claim 14 further comprising:
a cardboard shipping box sized to receive the container; and
an opening in a side of the cardboard shipping box positioned in alignment with the first small opening assembly in the container.

19. The apparatus of claim 18 further comprising:
a first set of hook or loop fastening material located on an exterior of the container adjacent to the first small opening assembly; and
a second set of hook or loop fastening material located on an interior of the cardboard shipping box and adjacent to the opening such that the first small opening assembly is mechanically held next to the opening in the carboard shipping box.

20. The apparatus of claim 18 wherein the opening in the side of the cardboard shipping box is formed from a three-sided flap cut into the cardboard shipping box.

21. The apparatus of claim 14 wherein the container is a soft-sided container.

22. The apparatus of claim 21 wherein the soft-sided container is a bag.

23. The apparatus of claim 22 wherein the second larger opening assembly comprises a roll-down opening.

24. The apparatus of claim 23 wherein the roll-down opening is held closed with hook and loop fasteners.

25. The apparatus of claim 14 wherein the container is a hard-sided container.

26. The apparatus of claim 25 wherein the hard-sided container is comprised of a hard case with a bottom and a top and wherein the second larger opening assembly is comprised of the opening formed when the top is rotated away from the bottom.

27. The apparatus of claim 14 wherein the first small opening assembly is separate from the second larger opening assembly.

* * * * *